(12) United States Patent
Solomon et al.

(10) Patent No.: US 6,210,379 B1
(45) Date of Patent: Apr. 3, 2001

(54) NEEDLE ASSEMBLY HAVING AN ELONGATED BLUNTING DEVICE WHICH ALLOWS FOR VENTING OF AIR

(75) Inventors: Donald D. Solomon, Southlake; Joseph J. Chang, Irving, both of TX (US); Phil D. Schmidt, Social Circle, GA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/452,848

(22) Filed: Dec. 2, 1999

(51) Int. Cl.[7] .................................................. A61M 5/00
(52) U.S. Cl. .............. 604/272; 604/164.01; 604/164.02; 604/164.06
(58) Field of Search .............................. 604/272, 164.01, 604/164.02, 164.06, 190, 158, 39, 43, 900, 523

(56) References Cited

U.S. PATENT DOCUMENTS

| | | | |
|---|---|---|---|
| 4,610,671 | 9/1986 | Luther | 604/168 |
| 4,619,643 | 10/1986 | Bai | 604/43 |
| 4,828,547 | 5/1989 | Sahi et al. | 604/158 |
| 5,009,642 | 4/1991 | Sahi | 604/158 |
| 5,201,712 | 4/1993 | Bryant | 604/164 |
| 5,472,430 | 12/1995 | Vaillancourt et al. | 604/198 |
| 5,540,662 | 7/1996 | Nicholson | 604/110 |
| 5,743,882 | 4/1998 | Luther | 604/168 |

*Primary Examiner*—John D. Yasko
(74) *Attorney, Agent, or Firm*—Blakely, Sokoloff, Taylor & Zafman (57) ABSTRACT

The invention generally relates to a needle assembly of the kind having a needle, an elongate blunting device, a shifting member, and a flash chamber. The needle is of the kind that has a needle proximal end, a sharp needle distal end and a needle canula extending therethrough. The elongate blunting device is at least partially located within the needle canula. The elongate blunting device is of the kind that has a blunting device proximal end, a blunting device distal end, and a blunting device blood flow passage therethrough through which blood can flow from the blunting device distal end to the blunting device proximal end. The shifting member can be actuated to move relative to the needle and, upon movement relative to the needle, causes movement to the elongate blunting device from a retracted position wherein the blunting device distal end is retracted into the needle canula so that the sharp needle distal end can penetrate the body, to an extended position wherein the blunting device distal end extends out of the needle canula so as to prevent the sharp needle distal end from penetrating the body. The flash chamber is of the kind that has an internal volume which in communication with the blunting device blood flow passage so that the blood can flow from the blunting device blood flow passage into the internal volume. The flash chamber is at least partially made of a material through which blood can be seen when located in the internal volume.

23 Claims, 9 Drawing Sheets

NEEDLE ASSEMBLY HAVING AN ELONGATED BLUNTING DEVICE WHICH ALLOWS FOR VENTING OF AIR

BACKGROUND OF THE INVENTION

1). Field of the Invention

This invention relates to a needle assembly having a needle with a sharp needle distal end, and an elongate blunting device which can be used to prevent penetration trauma by the sharp needle distal end.

2). Discussion of Related Art

Needle assemblies are used for various medical purposes such as withdrawing fluids from a body of a person, in particular blood from a vein or an artery, providing fluids to a body of a person or for inserting an object such as a catheter into a vein or an artery.

A needle assembly includes a needle having a sharp needle distal end. The sharp needle distal end is used to pierce a body and is inserted into fluids in the body. Body fluids may include viruses which can transfer diseases to medical personnel. Once the needle is removed from the body, care should be taken that the sharp needle distal end does not penetrate into the body of any medical personnel.

An elongate blunting device may be used for preventing penetration trauma of such a sharp needle distal end. The elongate blunting device may be located within a needle cannula of the needle and be moveable by a shifting member from a retracted position wherein a blunting device distal end of the elongate blunting device is retracted into the needle cannula, to an extended position wherein the blunting device distal end extends out of the needle cannula, thereby preventing the sharp needle distal end from penetrating the body of any medical personnel.

A blood flow passage can be provided through the needle and a flash chamber may be in communication with the blood flow passage so that blood can flow from the blood flow passage into an internal volume of the flash chamber. The flash chamber is typically made of a material through which blood can be seen when located within the internal volume. Medical personnel can then see when the sharp needle distal end pierces a vein or artery because blood would then flow from the sharp needle distal end into the internal volume of the flash chamber. In order for blood to flow from the sharp needle distal end into the flash chamber it is required that air located within passages within the needle assembly be vented out of these passages. The present invention primarily concerns itself with venting of air from such passages.

SUMMARY OF THE INVENTION

The invention generally relates to a needle assembly of the kind having a needle, an elongate blunting device, a shifting member, and a flash chamber. The needle is of the kind that has a needle proximal end, a sharp needle distal end and a needle cannula extending therethrough. The elongate blunting device is at least partially located within the needle cannula. The elongate blunting device is of the kind that has a blunting device proximal end, a blunting device distal end, and a blunting device blood flow passage therethrough through which blood can flow from the blunting device distal end to the blunting device proximal end. The shifting member can be actuated to move relative to the needle and, upon movement relative to the needle, causes movement to the elongate blunting device from a retracted position wherein the blunting device distal end is retracted into the needle cannula so that the sharp needle distal end can penetrate the body, to an extended position wherein the blunting device distal end extends out of the needle cannula so as to prevent the sharp needle distal end from penetrating the body. The flash chamber is of the kind that has an internal volume which in communication with the blunting device blood flow passage so that the blood can flow from the blunting device blood flow passage into the internal volume. The flash chamber is at least partially made of a material through which blood can be seen when located in the internal volume.

According to one aspect of the invention, an air venting passage is provided in the blunting device proximal end through which air can be vented from the blunting device blood flow passage substantially in a direction in which blood flows through the blunting device blood flow passage.

The air venting passage may, for example, be an air venting opening having dimensions which allow air through but which substantially prevent blood through. Alternatively, the air venting passage may be provided by a porous member which allows air through but which substantially prevents blood through.

According to another aspect of the invention an air venting passage is provided through which air can be vented from the blunting device blood flow passage. When blood flows into the blunting device blood flow passage, the air venting passage substantially prevents the blood from flowing therethrough.

According to another aspect of the invention the elongate blunting device may include an elongate blunting member and a blunt holding member. The elongate blunting member is at least partially located within the needle cannula and has a blunting member proximal end, a blunting member distal end, and a blunting member blood flow passage through which blood can flow from the blunting member distal end to the blunting member proximal end. The elongate blunting member has a blunting member blood exit opening through which the blood can flow out of the blunting member blood flow passage. The blunt holding member is secured to the proximal end of the elongate blunting member and has a surface facing the blunting member blood exit opening with a cavity defined between the surface and the blunting member exit opening so that blood can flow into the cavity. The internal volume of the flash chamber is in communication with the cavity so that blood can flow from the cavity into the internal volume.

BRIEF DESCRIPTION OF THE DRAWINGS

The invention is further described by way of examples with reference to the accompanying drawings wherein like references indicate like components and wherein.

DESCRIPTION OF PREFERRED EMBODIMENTS

Figure 1:
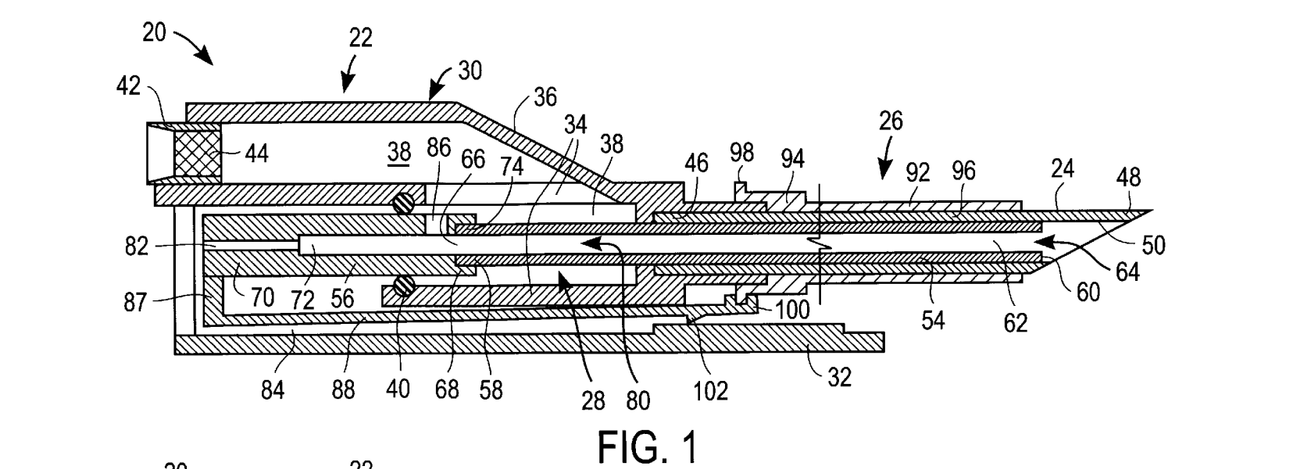
FIG. 1 is a sectioned side view of a needle assembly according to one embodiment of the invention, wherein an elongate blunting device thereof is located in a retracted position.

FIG. 1 of the accompanying drawings illustrates a needle assembly 20 which includes a main body 22, a needle 24, a catheter component 26, and an elongate blunting device 28.

The main body 22 includes a flash chamber 30, and an external ledge 32. The flash chamber 30 is formed by first and second tubular portions 34 and 36 respectively. The first and second tubular portions 34 and 36 are in communication with one another so as to define a continuous internal volume 38. The entire flash chamber 30 is made of a transparent or translucent plastics material through which blood can be seen when located within the internal volume 38. A proximal end of the first tubular portion 34 is open and a seal in the form of an O-ring 40 is located in a mouth of a proximal end of the first tubular portion 34. A proximal end of a second tubular portion 36 is open. A plug 42 is inserted into and closes off the proximal end of the second tubular portion 36. A core 44 of the plug 42 is made up of a porous material which can allow air through that which substantially prevents blood through. The core 44 typically has pore sizes of about 50 micron.

The needle 24 has a needle proximal end 46 and a sharp needle distal end 48. The needle proximal end 46 is secured to a distal end of the first tubular portion 46. A cannula 50 is formed through the needle 24 and an opening is formed in the distal end of the first tubular portion 34 so that the needle cannula 50 is in communication with the internal volume 38 in the first tubular portion 34.

The elongate blunting device 28 includes an elongate blunting member 54 and a blunt holding member 56. The elongate blunting member 54 has a blunting member proximal end 58 and a blunting member distal end 60. A blunting member blood flow passage 62 is formed through the elongate blunting member 54. The blunting member blood flow passage 62 has a blunting member blood entry opening 64 at the blunting member distal end 60, and a blunting member blood exit opening 66 at the blunting member proximal end 58.

The blunt holding member 56 has a blunt holding member distal end 68 and a blunt holding member proximal end 70. A blunt holding member blood flow passage 72 is formed into the blunt holding member distal end 68. A blunting member receiving opening 74 is also formed in the blunt holding member distal end 68. The blunting member receiving opening 74 is slightly larger in diameter and shorter than the blunt holding member blood flow passage 72. The blunting member proximal end 58 is inserted into the blunting member receiving opening 74. The blunting member proximal end 58 fits into the blunting member receiving opening 74 with a friction fit or a transition fit. The blunting member distal end 60 thereby forms a blunting device distal end 60 of the elongate blunting device 28, and the blunt holding member proximal end 70 forms a blunting device proximal end 70 of the elongate blunting device 28. The blunting member blood flow passage 62 and the blunt holding member blood flow passage 72 jointly form a blunting device blood flow passage 80 through the elongate blunting device 28.

An air venting passage in the form of an air venting opening 82 is formed in the blunting device proximal end 70. The air venting opening 82 extends in a direction in which the blunting device blood flow passage 80 extends. The blunting device blood flow passage 80 has a center line, and the air venting opening 84 has a center line which substantially coincides with the center line of the blunting device blood flow passage 80. The air venting opening 82 has a cross-dimension, or a diameter, which is sufficient for air to be vented therethrough, but is small enough so as to substantially prevent blood from flowing therethrough. The diameter of the air venting opening 84 is typically about 250 micron or less and typically has a length of about 2.5 mm.

A blood exit passage 86 is formed in a side of the blunt holding member 56 and extends from the blunt holding member blood flow passage 72 out of the blunt holding member 56.

The blunting member distal end 60 is inserted from the proximal end of the first tubular portion 34 through the O-ring 40 and from there into the needle cannula 50. The O-ring 40 is located and seals on an outer surface of the blunt holding member 56. The blunt holding member blood flow passage 72 is placed in communication with the internal volume 38 via the blood exit passage 86.

As shown in FIG. 1, the elongate blunting device 28 is located in a retracted position wherein the blunting member distal end 60 is retracted into the needle cannula 50.

A shifting member 84 is secured to the blunting device proximal end 70. The shifting member 84 includes a first portion 87 extending away from the blunt holding member 56, and a second portion 88 extending from the first portion 87 to the catheter component 26. The shifting member 84 has a clip formation 90. The shifting member 84 is bent against spring action thereof towards the flash chamber 30 and kept in such a position by the external ledge 34 with the clip formation 90 located against the external ledge 32.

The catheter component 26 includes a catheter 92 and a luer 94. A proximal end of the catheter 92 is secured to a distal end of the luer 94. The catheter component 26 has a catheter passage 96 formed therethrough. The needle 24 is inserted into the catheter passage 96 so that the catheter component 26 is located around the needle 24.

The luer 94 has a luer lock formation 98 which engages with a complementary locking formation 100 on a distal end of the shifting member 94. The catheter component 26 is thus connected via the shifting member 84 to the elongate blunting device 28. Movement of the catheter component along the needle 24 causes corresponding movement of the elongate blunting member 64 along the needle 24.

In use the sharp needle distal end 48 is used to pierce a body such as a vein or an artery of a person. The needle 24 and the catheter 92 are then inserted into the body together. The blunting device blood flow passage 80 and the internal volume 38 are initially filled with air. Blood flows into the needle cannula 50 of the sharp needle distal end 48 when the sharp needle distal end 48 pierces a vein or an artery. The blood flows from the needle cannula 50 through the blunting member blood entry opening 64 into the blunting member blood flow passage 62. The blood creates a pressure on the air located in the blunting device blood flow passage 80. The air enters the air venting opening 82 in the same direction that the blood flows into the blunting member blood flow passage 62. The air then flows through the air venting opening 82 and leaves the air venting opening 82 in the same direction as the direction in which the air enters the air venting opening 82. The air is so efficiently vented to atmosphere. The blood continues to flow into the blunting device blood flow passage 80 from the blunting member distal end 60 to the blunt holding member proximal end 70 until all the air located within the blunting device blood flow passage 80 is vented through the air venting opening 82 and the entire blunting device blood flow passage 80 is filled with blood.

Because of the dimensions of the air venting opening 82, the blood within the venting device blood flow passage 80 is prevented from flowing through the air venting opening 82. The blood flows from the blunting device blood flow passage 80 through the blood exit passage 86 into the internal volume 38. A leaktight interface between the blunt holding member 56 and the O-ring 40 prevents blood from leaking past the blunt holding member 56. The blood creates a pressure on the air located within the internal volume 38. The air is vented through the core 44 of the plug 42 due to the porous nature of the core 34. The blood continues to flow through the internal volume 38 until all the air is vented through the core 44 and the entire internal volume 38 is filled with blood. The blood is, however, prevented from flowing through the core 44 of the plug 42. Because of the transparent or translucent material of the flash chamber 30, a person can then see the blood located within the internal volume 38, thus allowing the person to determine when the sharp needle distal end 48 pierces a vein or artery.

Figure 2:
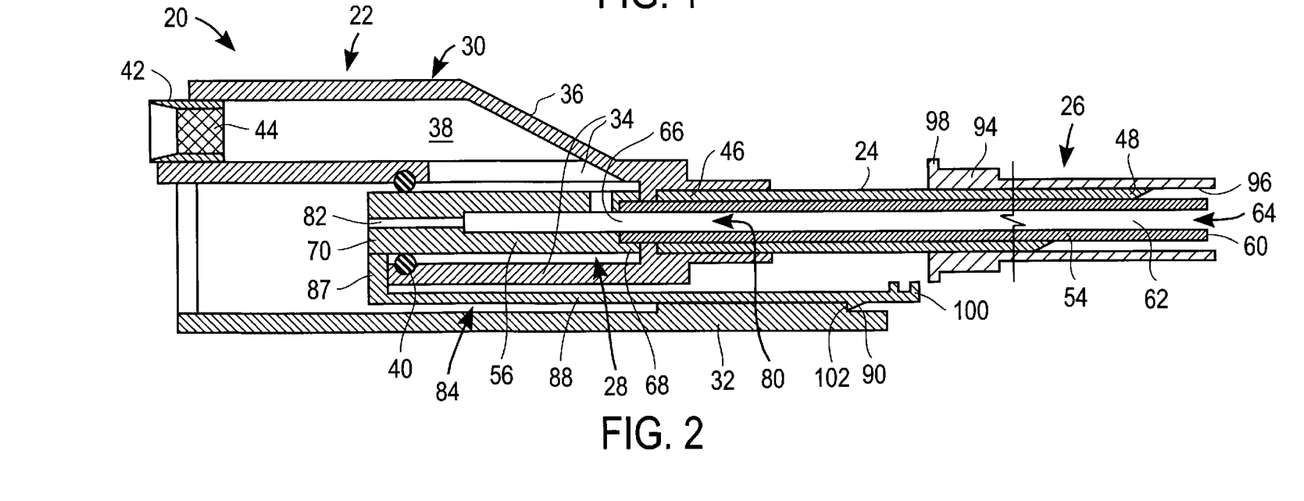
FIG. 2 is a view similar to FIG. 1 wherein the elongate blunting device is in an extended position.

Once the catheter 92 is located in a required position, the needle 24 is pulled out of the catheter component 26 as shown in FIG. 2. The O-ring 40 slides on a surface of the blunt holding member 56 thus allowing for movement of the elongate blunting device 28 relative to the flash chamber 30. Because of a connection between the catheter component 26 and the elongate blunting device 28, the elongate blunting member 54 remains in a substantially stationery location relative to the catheter 92 when the needle 24 is partially removed from the body and partially out of the catheter 92. The elongate blunting member 44 thereby moves relative to the needle 24 from the retracted position to an extended position wherein the blunting member distal end 60 extends out of the needle cannula 50. The shifting member 84 is thus actuated by the catheter component 26 to move relative to the needle 24 and, upon movement relative to the needle 24, causes movement of the elongate blunting member 54 from the retracted position to the extended position.

While the needle 24 is moved out of the catheter 92, the clip formation 90 slides along the external ledge 32. The clip formation 90 ultimately snaps into position behind a complementary formation 102 and the external ledge 32 due to spring action of the shifting member 84. The locking formation 100 moves away from the luer lock formation 98 thus disconnecting the catheter component 26 from the shifting member 84. The needle 24 and the elongate member are then together removed out of the catheter component 26 while the catheter 92 remains within the body.

Figure 3:
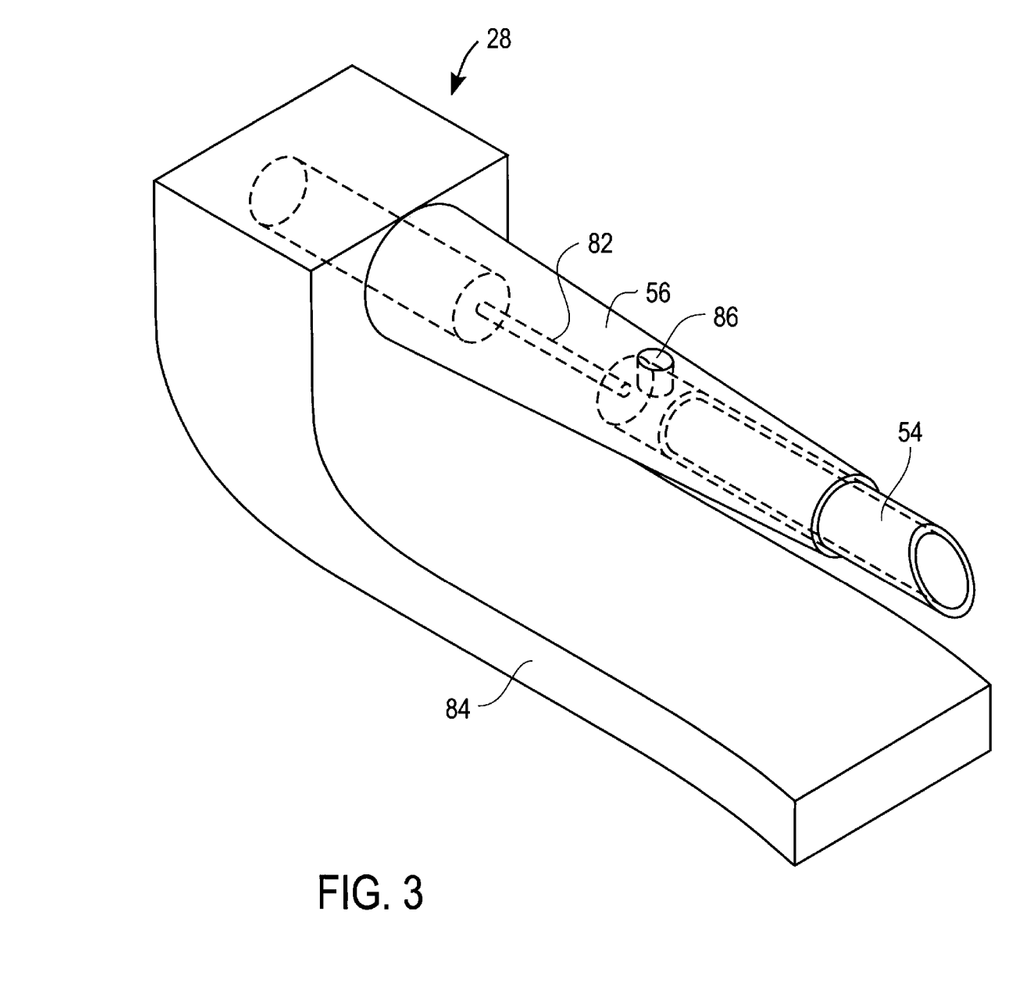
FIG. 3 is a perspective view of the elongate blunting device of FIG. 1 showing in more detail a blood exit passage.

After the needle 24 and the elongate blunting member 54 are moved out of the catheter component 26, the blunting member distal end 60 prevents the sharp needle distal end 48 from penetrating another body. The elongate blunting member 54 is prevented from moving out of the extended position because of the clip formation 90 which engages with the formation 102 on the external ledge 32. The needle assembly 20 can then be safely dispensed of with a substantially reduced likelihood that the sharp needle distal end 48 would cause penetration trauma FIG. 3 illustrates a portion of the elongate blunting device 28 and the shifting member 84. The air venting opening 82 is a micro hole which may be injection molded at the time when the blunt holding member 56 and the shifting member 84 are molded. Alternatively, the air venting opening 82 may be a micro hole which is lazer drilled after the blunt holding member 56 and the shifting member 84 are molded.

Figure 4:
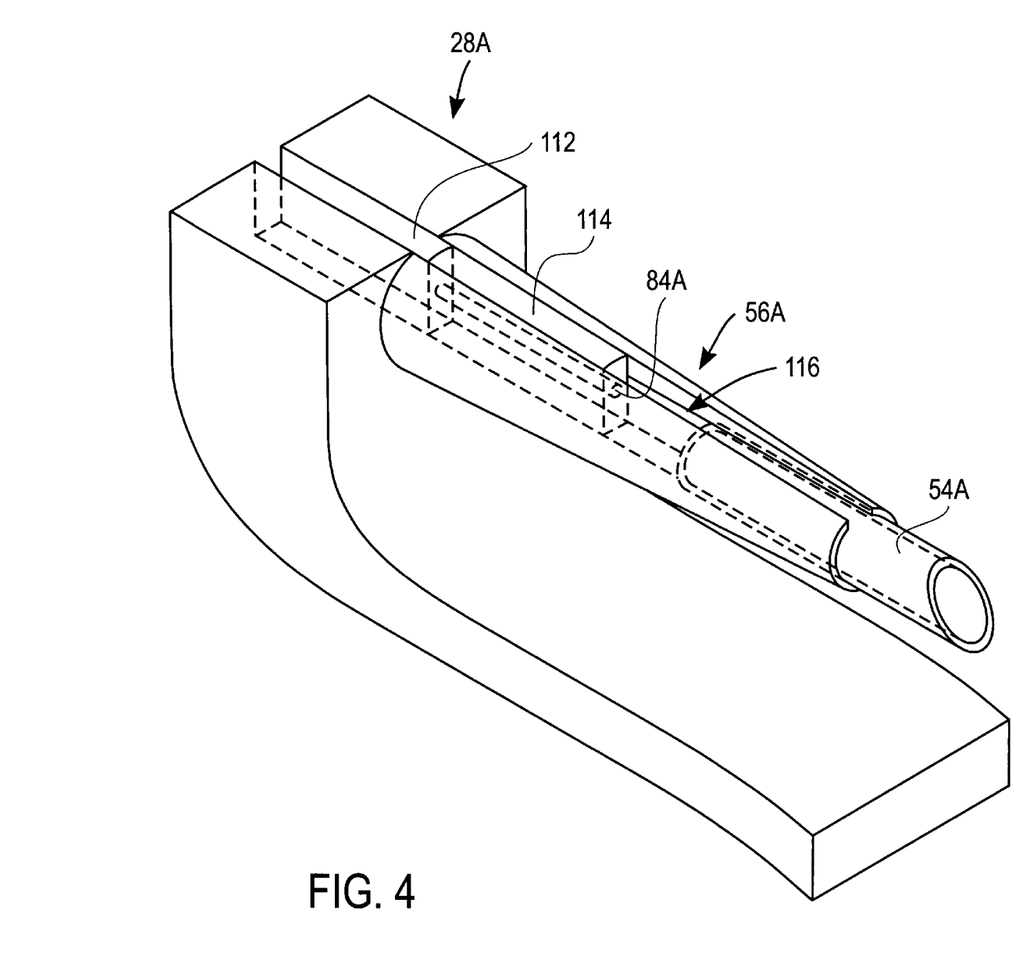
FIG. 4 is a perspective view of an elongate blunting device having a passage forming member which is inserted into a slot of a blunt holding member.

FIG. 4 illustrates a portion of an elongate blunting device 28A according to an alternative embodiment of the invention. The elongate blunting device 28A includes a blunt holding member 56A and an elongate blunting member 54A as in the embodiment hereinbefore described. A slot 112 is formed in the side of the blunt holding member 56A. The elongate blunting device 28A further includes a passage forming member 114. The passage forming member 114 has an air venting opening 84A therethrough. The air venting opening 84A is a micro hole which may be lazer drilled or injection molded in the passage forming member 114.

The passage forming member 114 is inserted into the slot 112 with a friction fit or a transition fit. The passage forming member 114 is thereby secured to the blunt holding member 56A in a position wherein a blood channeling cavity 116 is defined by surfaces of the slot 112 in the blunt holding member 56A and by a surface of the passage forming member 114. Blood flows from the elongate blunting member 54A into the blood channeling cavity 116 and from the blood channeling cavity into the internal volume (reference numeral 38 in FIG. 1) of the flash chamber (reference numeral 40 in FIG. 1).

An advantage of the elongate blunting device 28A of FIG. 4 is that it can be easily to manufactured by separately manufacturing the blunt holding member 56A and the passage forming member 114, and manufacturing the air venting opening 82A under more controlled conditions.

Figure 5:
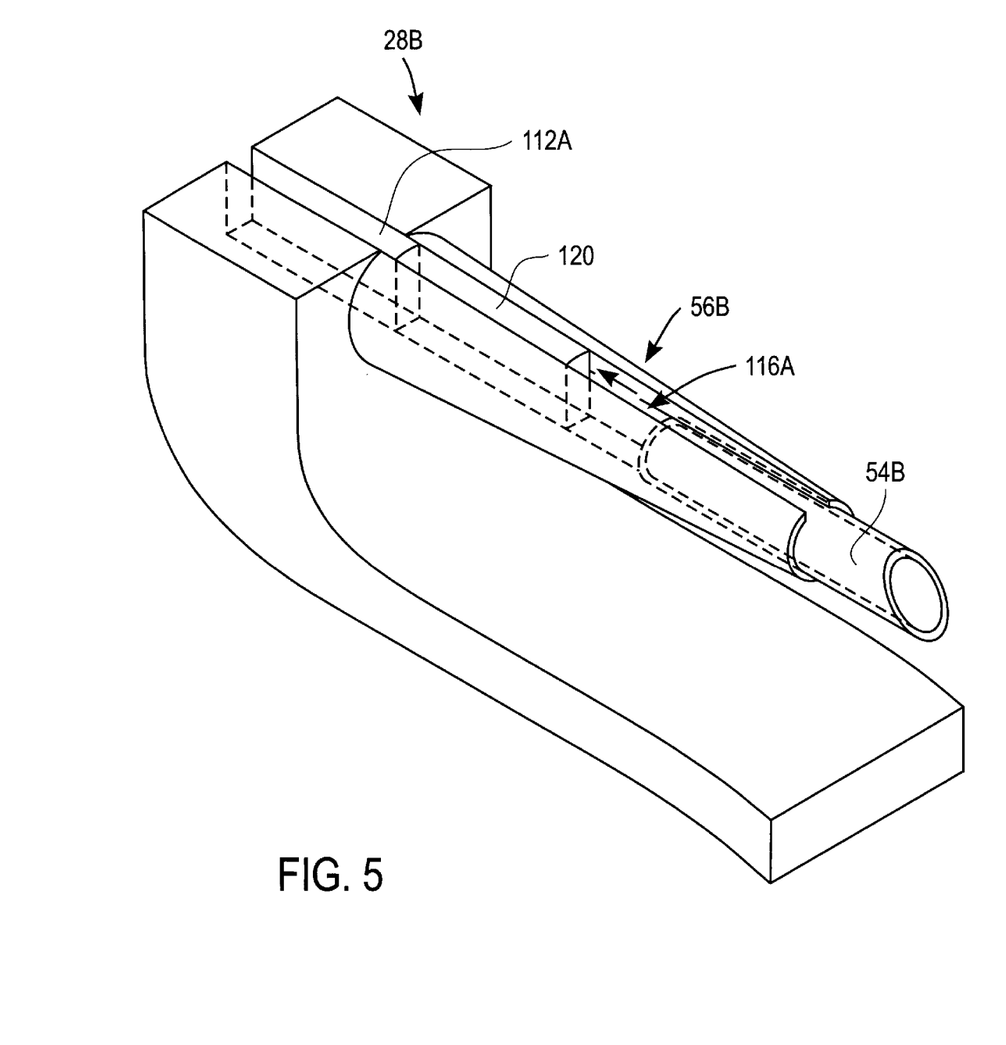
FIG. 5 is a perspective view of an elongate blunting device having a porous plug which is inserted into a slot of a blunt holding member, the porous plug serving as an air venting passage.

FIG. 5 illustrates an elongate blunting device 28B according to another embodiment of the invention. The elongate blunting device 28B also includes a blunt holding member 26B and an elongate blunting device 54B. As with the embodiment of FIG. 4, the blunt holding member 26B has a slot 112A. The elongate blunting device 28B further includes a porous plug 120. The porous plug 120 is inserted into the slot 112 with a friction fit or a transition fit. The porous plug 120 is thereby secured to the blunt holding member 56B so that a blood channeling cavity 116A is defined by surfaces of the slot 112 and a surface of the porous plug 120.

Blood flows from the elongate blunting member 54B into the blood channeling cavity 116A. The porous plug 120 is made of a porous material which allows air through but substantially prevents blood through. The porous plug 120 typically has pore sizes of about 50 micron a length of about 2.5 mm and a width of about 1 mm. Air can thus be vented through the porous plug 120 to atmosphere. The porous plug 120 thereby defines an air venting passage through which the air is vented, but substantially prevents the blood from flow pass through. The blood flows from the blood channeling cavity 116A to an internal volume of a flash chamber.

Figure 6:
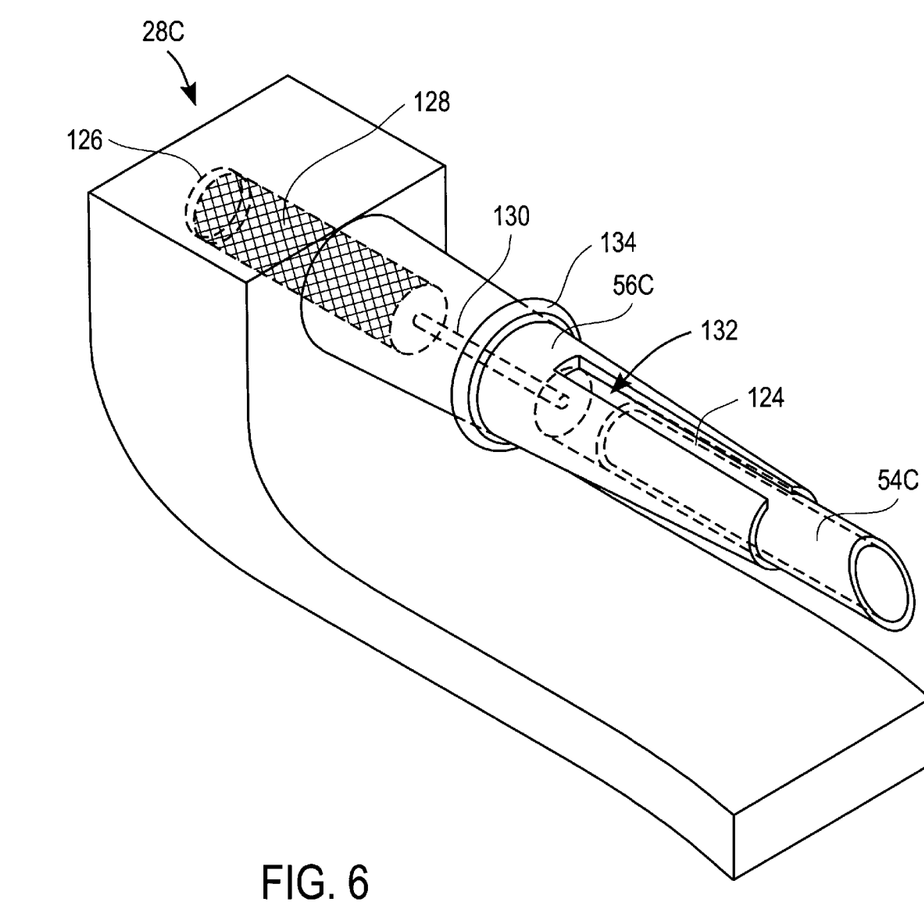
FIG. 6 is a perspective view of an elongate blunting device having a porous plug inserted into a proximal end of a blunt holding member.

FIG. 6 illustrates an elongate blunting device 28C according to yet a further embodiment of the invention. The elongate blunting device 28C, as in the embodiment hereinbefore described, includes a blunt holding member 56C and an elongate blunting member 54C secured thereto. A slot 124 is formed in the side of the blunt holding member 56C. The slot 124 is "blind" in the sense that the slot is formed only in a distal end of the blunt holding member 56C.

A blunt opening 126 is formed into a proximal end of the blunt holding member 56C. The blunt opening 126 extends into the blunt holding member 56C substantially in a direction opposite to the direction in which blood flows through the elongate blunting member 54C. A porous plug 128 is inserted into the plug opening 126 in a direction opposite to the direction in which the blood flows through the elongate blunting member 54C. An air connection opening 130 interconnects the slot 124 and the blunt opening 126. A blood channeling opening is defined within the confines of a distal surface of the porous plug 128, a surface of the opening 130, and surfaces of the slot 132. Air is vented through the blood channeling cavity 132, and then through the porous plug 128 due to the porous nature thereof. The blood is however prevented from passing through the porous plug 128. The blood flows from the blood channeling cavity 132 to an internal volume of a flash chamber.

As shown in FIG. 6, an O-ring 144 may be located in a stationary position around the blunt holding member 56C. The O-ring 144 is slideably engaged and seals with a flash chamber. Movement of the elongate blunting device 128 relative to a needle causes sliding movement of the O-ring 144 against a surface of a flash chamber. The embodiments hereinbefore described may utilize a similar O-ring 144 instead of an O-ring such as the O-ring 40 in FIG. 1 which slides on the blunt holding member 56.

Figure 7:
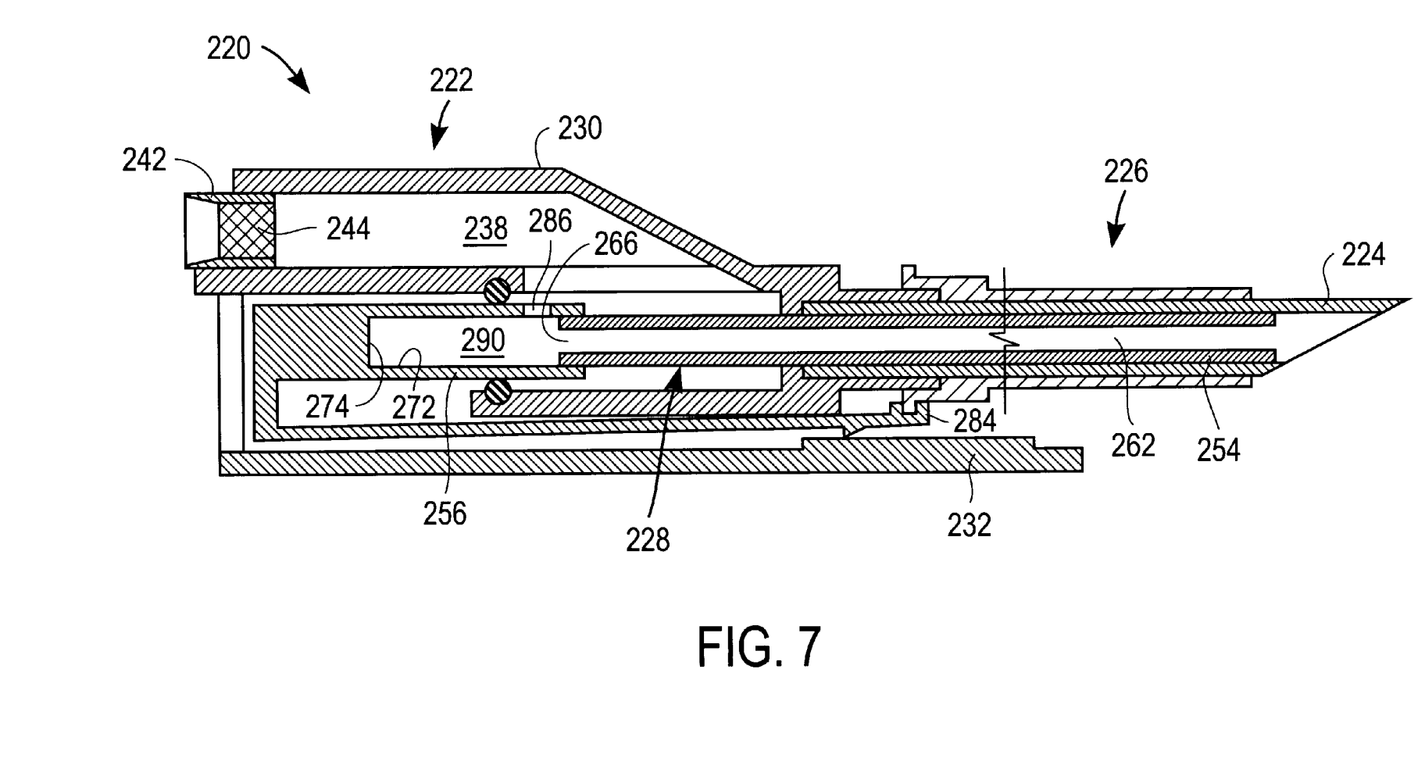
FIG. 7 is a sectioned side view of a needle assembly according to an alternative embodiment of the invention.

FIG. 7 illustrates a needle assembly 220 according to an alternative embodiment of the invention. As with the needle assembly 20 of FIG. 2, the needle assembly 220 includes a main body 222, a needle 224, a catheter component 226, an elongate blunting device 228, an external ledge 232, and a shifting member 284. The elongate blunting device 228 includes an elongate blunting member 254, and a blunt holding member 256. A blunt holding member blood flow passage 272 is formed in the blunt holding member 256. A proximal end of the elongate blunting member 254 is inserted into the blunt holding member blood flow passage 272. No air venting passage is provided such as the air venting opening 82 in the embodiment of FIG. 1. Instead, the blunt holding member 256 has an internal surface 274 facing a blunting member blood exit opening 266 of a blunting member blood flow passage 262 in the elongate blunting member 254. A cavity 290 is defined between the surface 274 and a proximal end of the elongate blunting member 254. Air is vented through an exit passage 286 in a side of the blunt holding member 256 to an internal volume 238 in a flash chamber 230 and through a core 244 of a plug 242. The embodiment of FIG. 7 is the same as the embodiment of FIG. 1 in all other respects.

Figure 8:
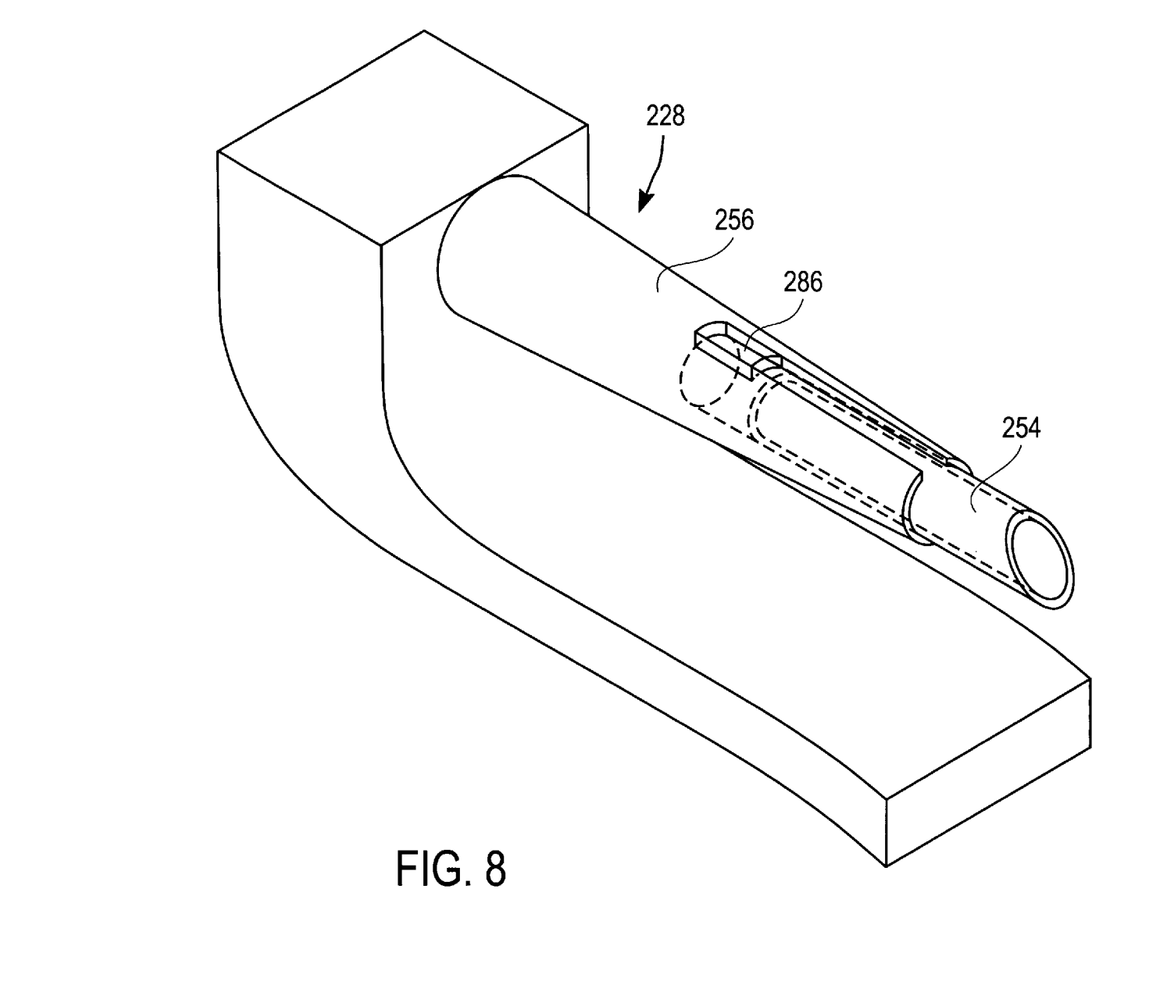
FIG. 8 is a perspective view of an elongate blunting device which is used in the needle assembly of FIG. 7.

FIG. 8 illustrates the elongate blunting device 228 of FIG. 7 in more detail. It can be seen that the exit opening 286 is entirely defined and circumscribed by the blunt holding member 256.

Figure 9:
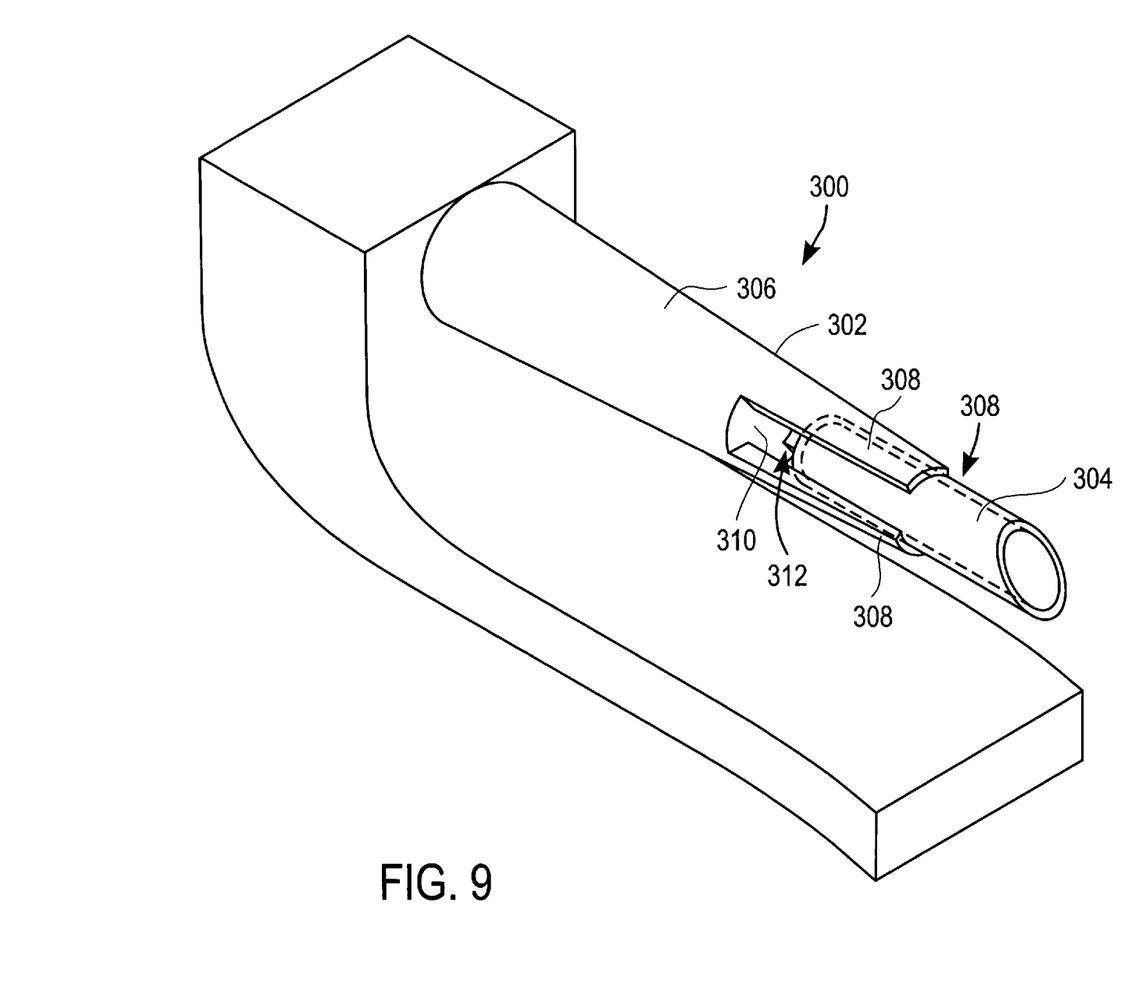
FIG. 9 is a perspective view of an elongate blunting device including a blunt holding member having claws which engage with an elongate blunting member.

FIG. 9 illustrates an elongate blunting device 300 according to a further embodiment of the invention. The elongate blunting device 300 includes a blunt holding member 302 and an elongate blunting member 304.

The blunt holding member 302 includes a proximal main support portion 306 and three claws 308 extending from the main support portion 306. The main support portion 306 has a surface located between the claws 308. A proximal end of the elongate blunting member 304 is inserted between the claws 308. The claws 308 engage with the elongate blunting member 304 on three different sides thereof.

A cavity 312 is defined between the surface 310 and the proximal end of the elongate blunting member 304. Blood flows from the elongate blunting member 304 into the cavity 312. Three exit openings are defined between respective pairs of the claws 308 so the blood can flow from the cavity 312 through the exit openings out of the elongate blunting device 300.

Figure 10:
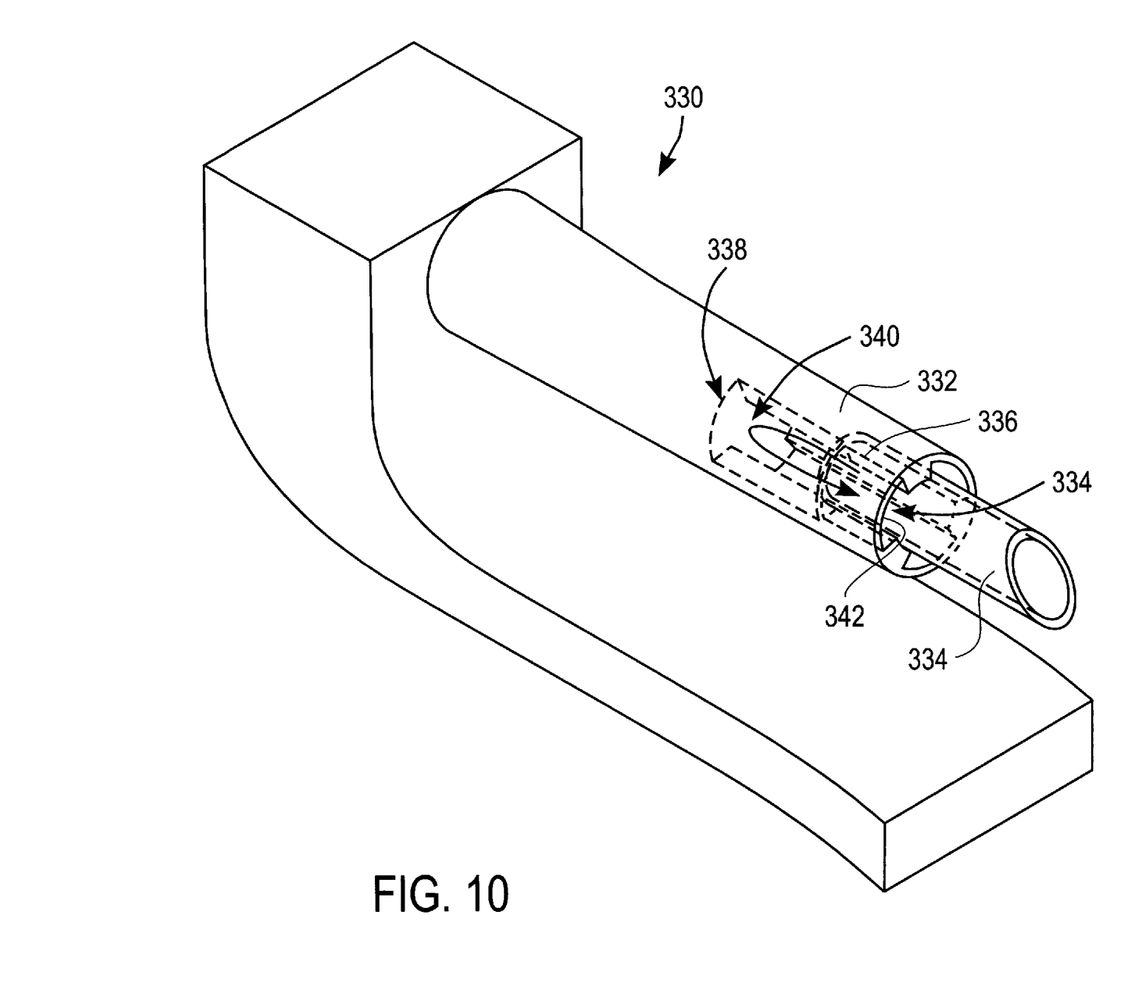
FIG. 10 is a perspective view of an elongate blunting device which includes a blunt holding member having a blunt receiving opening into which an elongate blunting member is inserted, the opening having grooves which define exit passages through which blood can flow.

FIG. 10 illustrates a further embodiment of an elongate blunting device 330 according to the invention. The elongate blunting device 330 includes a blunt holding member 332 and an elongate blunting member 334. A blunt receiving opening 336 is formed into a distal end of the blunt holding member 332. The blunt holding member 332 has a surface 338 in a base of the blunt holding opening 336.

A proximal end of the elongate blunting member 334 is inserted into the blunt receiving opening 336. A cavity 340 is defined between the proximal end of the elongate blunting member 334 and the surface 338. Blood can flow into the cavity 340.

Three grooves 342 are formed on a surface of the blunt receiving opening 336 facing a side of the elongate blunting member 334. Each groove 342 allows for a respective blood exit passage 344 to be defined between a side surface of the elongate blunting member 334 and an inner surface of the blunt holding member 332. Blood can flow from the cavity 340 through each blood exit passage 344 out of the elongate blunting device 330.

While certain exemplary embodiments have been described and shown in the accompanying drawings, it is to be understood that such embodiments are merely illustrative and not restrictive of the current invention, and that this invention is not restricted to the specific constructions and arrangements shown and described, since modifications may occur to those ordinarily skilled in the art.

What is claimed:

1. A needle assembly comprising:
   a needle having a needle proximal end, a sharp needle distal end, and a needle cannula extending therethrough;
   an elongate blunting device which is at least partially located within the needle cannula, the elongate blunting device having a blunting device proximal end, a blunting device distal end, a blunting device blood flow passage therethrough through which blood can flow from the a blunting device distal end to the a blunting device proximal end, and an air venting passage in the blunting device proximal end through which air can be vented from the blunting device blood flow passage substantially in a direction in which the blood flows through the blunting device blood flow passage;
   a shifting member which can be actuated to move relative to the needle and, upon movement relative to the needle, causes movement of the elongate blunting device from a retracted position wherein the blunting device distal end is retracted into the needle cannula so that the sharp needle distal end can penetrate a body, to and extend position wherein the blunting device distal end extends out of the needle cannula so as to prevent the sharp needle distal end from penetrating the body; and
   a flash chamber having an internal volume which is in communication with the blunting device blood flow passage so that the blood can flow from the blunting device blood flow passage into the internal volume, the flash chamber being at least partially made of a material through which the blood can be seen when located in the internal volume.

2. A needle assembly according to claim 1 wherein the air is vented through the air venting passage to atmosphere.

3. A needle assembly according to claim 2 wherein the air leaves the passage substantially in the direction in which the blood flows through the blunting device blood flow passage.

4. A needle assembly according to claim 1 wherein the blunting device blood flow passage has a center line, and the air venting passage has a center line which substantially coincides with the center line of the blunting device blood flow passage.

5. A needle assembly according to claim 1 wherein the air venting passage substantially prevents blood from flowing therethrough.

6. A needle assembly according to claim 5 wherein the air venting passage is an air venting opening.

7. A needle assembly according to claim 6 wherein the air venting opening has a cross-dimension of less than 250 micron.

8. A needle assembly according to claim 6 wherein the elongate blunting device includes:
   an elongate blunting member which is at least partially located within the needle cannula, the elongate blunting member having a blunting member distal end forming the blunting device distal end, and a blunting member proximal end;
   a blunt holding member secured to the blunting member proximal end; and
   a passage forming member secured to the blunt holding members, the passage forming member defining the air venting opening.

9. A needle assembly according to claim 8 wherein a slot is formed in a side of the blunt holding member and the passage forming member is inserted into the slot.

10. A needle assembly according to claim 8 wherein a blood channeling cavity is defined by surfaces of the blunt holding member and the passage forming member, the blood flowing into the blood channeling cavity from where the blood flows to the internal volume of the flash chamber.

11. A needle assembly according to claim 5 wherein the elongate blunting device includes an elongate blunting member which is at least partially located within the needle cannula, the elongate blunting member having a blunting member distal end forming the blunting device distal end, and a blunting member proximal end;
   a blunt holding member secured to the blunting member proximal end; and
   a porous member, the porous member being made of a porous material which allows air through but substantially prevents blood through, the porous member being positioned and formed so as to form the air venting passage by allowing the air to be vented therethrough due to the porous nature thereof but substantially preventing the blood from flowing therethrough.

12. A needle assembly according to claim 11 wherein the blunt holding member has a plug opening formed therein and the porous member is porous plug which is inserted into the plug opening.

13. A needle assembly according to claim 12 wherein the plug opening extends into the blunt holding members substantially in a direction opposite to the direction in which the blood flows through the blunting member blood flow passage so that the porous plug is inserted into the plug opening in a direction opposite to the direction in which the blood flows through the blunting members blood flow passage.

14. A needle assembly according to claim 12 wherein the plug opening is a slot in a side of the blunt holding member, and the porous plug is inserted into the slot.

15. A needle assembly according to claim 12 wherein a blood channeling cavity is defined by surfaces of the blunt holding member and the porous plug, blood flowing from the blood flow passage into the blood channeling cavity from where the blood flows to the internal volume of the flash chamber.

16. A needle assembly according to claim 1 which includes a clip formation which snaps into position when the elongate blunting device is moved into the extended position so that the elongate blunting member is prevented from moving out of the extended position towards the retracted position.

17. A needle assembly according to claim 1 which includes a catheter located around the needle, the catheter being insertable, together with the needle into the body, whereafter the needle can be removed from the body and out of the catheter while the catheter remains within the body.

18. A needle assembly according to claim 17 wherein the elongate blunting device is connected to the catheter so that, when the needle is partially removed from the body and partially out of the catheter, the elongate blunting device remains in a substantially stationary location relative to the catheter so that the elongate blunting device moves relative to the needle from the retracted position to the extended position, whereafter the elongate blunting device disconnects from the catheter to allow for movement of the elongate blunting device together with the needle out of the body while the catheter remains within the body.

19. A needle assembly according to claim 1 which includes a seal around the elongate blunting device and between the elongate blunting device and the flash chamber so as to substantially prevent leakage of blood out of the flash chamber.

20. A needle assembly according to claim 19 wherein the seal slides on a surface of the elongate blunting device when the elongate blunting device moves from the retracted position to the extended position.

21. A needle assembly according to claim 19 wherein the seal slides on a surface of the flash chamber when the elongate blunting device moves from the retracted position to the extended position.

22. A needle assembly according to claim 1 wherein the flash chamber has a plug aperture, and further comprising a porous plug which closes off the opening, the porous plug being made of a material that allows air through but substantially prevents blood through so that air is vented therethrough when the flash chamber fills with blood due to the porous nature thereof, but blood is substantially prevented from flowing therethrough out of the flash chamber.

23. A needle assembly comprising:
   a needle having a needle proximal end, a sharp needle distal end, and a needle cannula extending therethrough;
   an elongate blunting device which is at least partially located within the needle cannula, the elongate blunting device having a blunting member proximal end, a blunting device distal end, a blunting device blood flow passage therethrough through which blood can flow from the blunting device distal end to the blunting device proximal end, and an air venting passage through which air can be vented from the blunting device blood flow passage when the blood flows into the blunting device blood flow passage, the air venting passage substantially preventing the blood from flowing therethrough;

a shifting member which can be actuated to move relative to the needle and, upon movement relative to the needle, causes movement of the elongate blunting device from a retracted position wherein the blunting device distal end is retracted into the needle cannula so that the sharp needle distal end can penetrate a body, to an extended position wherein the blunting device distal end extends out of the needle cannula so as to prevent the needle from penetrating the body; and a flash chamber having an internal volume which is in communication with the blunting device blood flow passage so that the blood can flow from the blunting device blood flow passage into the internal volume, the flash chamber being at least partially made of a material through which the blood can be seen when located in the internal volume.

* * * * *